(12) United States Patent
Ilmoniemi et al.

(10) Patent No.: US 6,503,187 B1
(45) Date of Patent: Jan. 7, 2003

(54) STIMULATOR HEAD AND METHOD FOR ATTENUATING THE SOUND EMITTED BY A STIMULATOR COIL

(76) Inventors: Risto Ilmoniemi, Nuottarinne 4 A 2, FIN-02230 Espoo (FI); Jarmo Ruohonen, Sahatie 12 B 40, FIN-01650 Vantaa (FI); Janne Kamppuri, Tehtaankatu 20 B 23, FIN-00140 Helsinki (FI); Juha Virtanen, Suovatie 14 A, FIN-00660 Helsinki (FI)

( * ) Notice: Subject to any disclaimer, the term of this patent is extended or adjusted under 35 U.S.C. 154(b) by 0 days.

(21) Appl. No.: 09/554,812
(22) PCT Filed: Nov. 27, 1998
(86) PCT No.: PCT/FI98/00932
§ 371 (c)(1), (2), (4) Date: May 18, 2000
(87) PCT Pub. No.: WO99/27995
PCT Pub. Date: Jun. 10, 1999

(30) Foreign Application Priority Data

Nov. 28, 1997 (FI) .................................................. 974371

(51) Int. Cl.$^7$ ................................................. A61N 2/02
(52) U.S. Cl. ............................... 600/14; 600/9; 600/13; 607/1; 607/45
(58) Field of Search ............................ 607/1–3, 50–52, 607/68–76, 115, 139–141; 600/9–14

(56) References Cited

U.S. PATENT DOCUMENTS 4,112,923 A * 9/1978 Tomecek ..................... 600/11
5,545,996 A * 8/1996 Morich et al. .............. 324/318

FOREIGN PATENT DOCUMENTS

DE 296 14 403 12/1996
WO 97/22383 6/1997

* cited by examiner

Primary Examiner—David M. Shay
(74) Attorney, Agent, or Firm—Smith-Hill and Bedell

(57) ABSTRACT

The present invention relates to a stimulator head of a magnetic stimulator used in the stimulation of living tissue such as the human brain. Such a stimulator bead comprises a stimulator head body (3) suited for mounting the stimulator head on the magnetic stimulator equipment, at least one coil (1) which is connected to said stimulator head body (3) and is designed suitable for generating a stimulating magnetic field, and conductors (7) for passing electric current from said magnetic stimulator into any of said at least one coil (1). According to the invention, the stimulator head includes a housing (2) which is connected to said stimulator head body (3) and is designed to enclose at least one air-tight space (5) which further separates each of said at least one stimulator coil (1) from the other parts of said housing (2) facing the object being stimulated. Further according to the invention, each of said at least one coil (1) is placed in said housing (2), whereby an acoustic insulation can be attained between each of said at least one coil (1) and the object being stimulated by virtue of bringing the pressure in said air-tight space (5) to a substantially low level.

3 Claims, 3 Drawing Sheets

Figure 1:
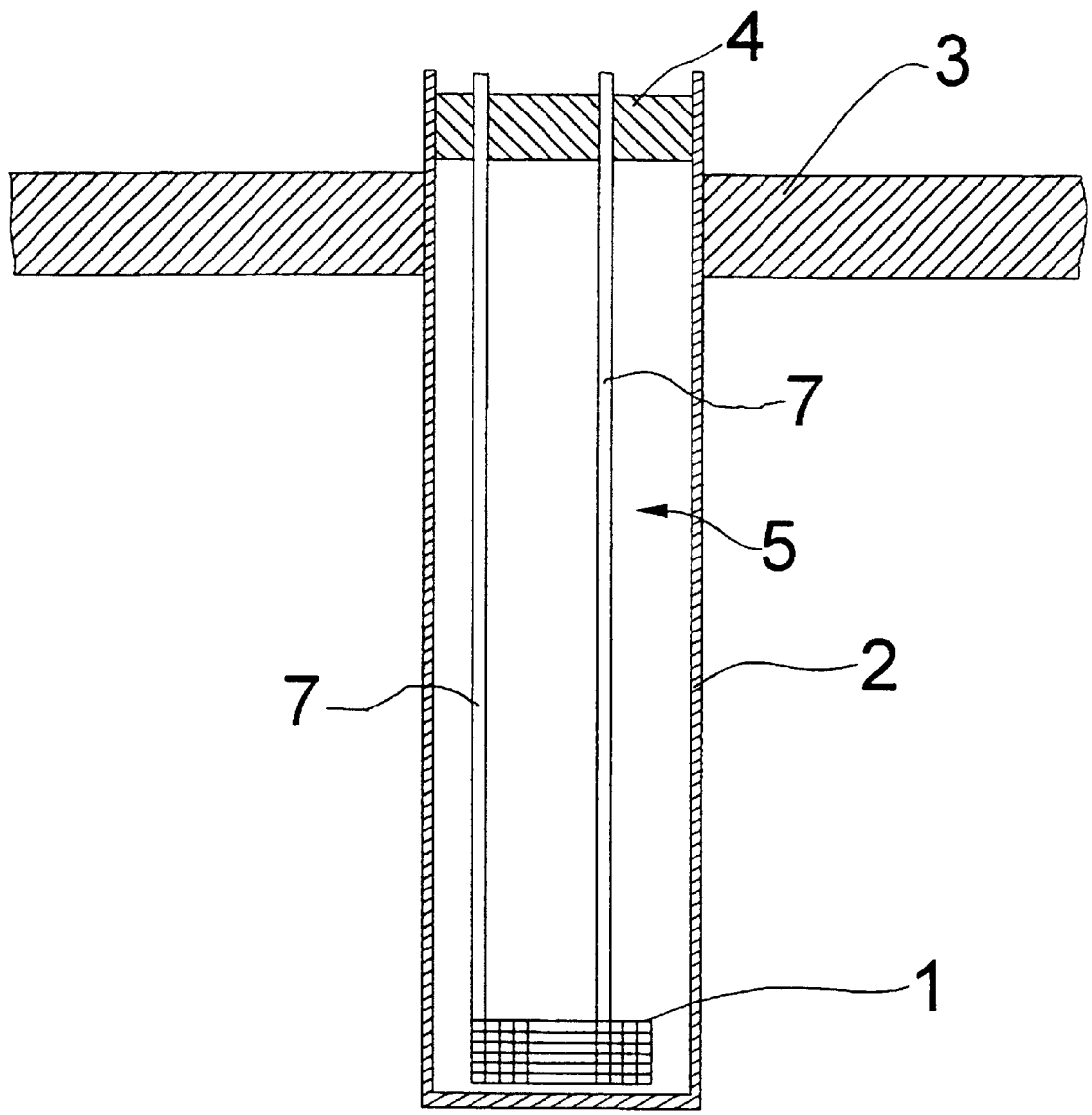

STIMULATOR HEAD AND METHOD FOR ATTENUATING THE SOUND EMITTED BY A STIMULATOR COIL

The present invention relates to a stimulator head according to the preamble of claim 1 and a method according to the preamble of claim 5.

Stimulator heads are used in magnetic stimulators as transducers of electric energy which is fed to the stimulator head from the stimulator power supply into magnetic field energy. The magnetic field is generated by means of a coil placed into the body of the stimulator head and, in some constructions, the stimulator head may form an integral part of the magnetic stimulator.

As known from the prior art, biological tissue and other conductive media can be excited by applying thereon an electromagnetic field composed of an electric field E and a magnetic field B. Thus, a plurality of different tissues such as the brain, the peripheral nervous system and the heart may be stimulated by means of an electric field. A suitable electromagnetic field can be induced using a coil placed, e.g., on the object to be stimulated.

The cerebral cortex can be stimulated without health risks and pain by applying with the help of one or more coils placed on the head a strong magnetic field that induces an electric current at a desired point. Activation of nerve cells by means of electric current applied thereon can be utilized in a plurality of different ways. For instance, the stimulation of certain cortical areas triggers the contraction of the muscles controlling the functions of the hand thus permitting the velocities of nerve conduction from the brain to the muscles to be measured. The stimulation of certain other areas can be employed to interfere with the normal function of the brain, e.g., during the execution of a given task thus allowing the cortical areas related to the execution of different tasks to be localized. Furthermore, the stimulation of certain areas of the brain may also have therapeutic effects; for instance, patients suffering from depression have been reported to gain relief from the stimulation of cortical areas of the frontal lobe.

Conventionally, the stimulating magnetic field is generated by means of a coil made from coiled loops of a large-diameter, cooled conductor. In order to generate the desired magnetic field, the magnetic stimulator coil is fed with a current pulse typically having a magnitude of 1–20 kA and a duration of 50–500 $\mu$s. The repetition rate of the current pulses may be, e.g, 0.1–50 Hz, and they are capable of inducing very strong forces of a rapid rate of change on the conductors. Due to such forces, the coil will be subjected to a massive mechanical shock emitting an acoustic wave with a spectrum typically including frequencies in the range 1–10 kHz and a sound level reaching up to 120 dB and above. The emitted acoustic wave can cause a hearing damage in the ear at the level of the hair cells of the inner ear. Conventionally, such countermeasures as ear plugs and other kind of hearing-protection devices have been used to guard against the acoustic wave. Despite the use of protective devices, the sound often is experienced annoying to both the patient or test person and the examination session operator. Moreover, the sound emitted in conjunction with the stimulation can activate brain areas associated with hearing, whereby the interpretation of brain activation tests will become more complicated. Particularly in research into the hearing system, the noise emitted by the stimulator coil is most disturbing.

It is an object of the invention to overcome the above-described drawbacks of the conventional techniques and to provide an entirely novel type of stimulator head for a magnetic stimulator and a method of attenuating the acoustic wave emitted by said stimulator coil.

The goal of the invention is attained by essentially housing the stimulator coil elements inside a structure which allows at least the stimulator coil proper to be enclosed by a shell taken to a vacuum. With the provision that the interior of the stimulator coil housing can be taken to an essentially complete vacuum, it is at least in principle possible to make a perfect acoustic shield. However, even such an arrangement in practice allows sound to some extend to be conducted to the surroundings via the suspension structures and current supply conductors of the coil. In addition to airtightness, the stimulator coil housing must be transparent to magnetic field at least for those parts separating the coil from the object being stimulated.

More specifically, the stimulator head according to the invention to be used in a magnetic stimulator is characterized by what is stated in the characterizing part of claim 1. Furthermore, the method according to the invention is characterized by what is stated in the characterizing part of claim 5.

The invention offers significant benefits. By virtue of the invention, it will be possible to make an essential improvement in the attenuation of the noise emitted by the stimulator toward the ears of the person being examined or the test session operator and in the overall disposition of the test environment. The sound attenuation technique according to the invention is capable of damping noise emission from the stimulator equipment to such a low level as to make it blend with the 50–60 dB background noise level which in most auditory tests is considered acceptably low. Then, the noise emitted by the stimulator coil does not any more cause a disturbance nor risk to the hearing of the test persons or the examination session operating personnel. The accuracy of stimulation tests performed by virtue of the invention on the brain and particularly on the hearing system will also be enhanced, because the invention makes it possible to avoid the undesirable activation of auditory cortical areas in conjunction with the application of the stimulation pulse.

Figure 2:
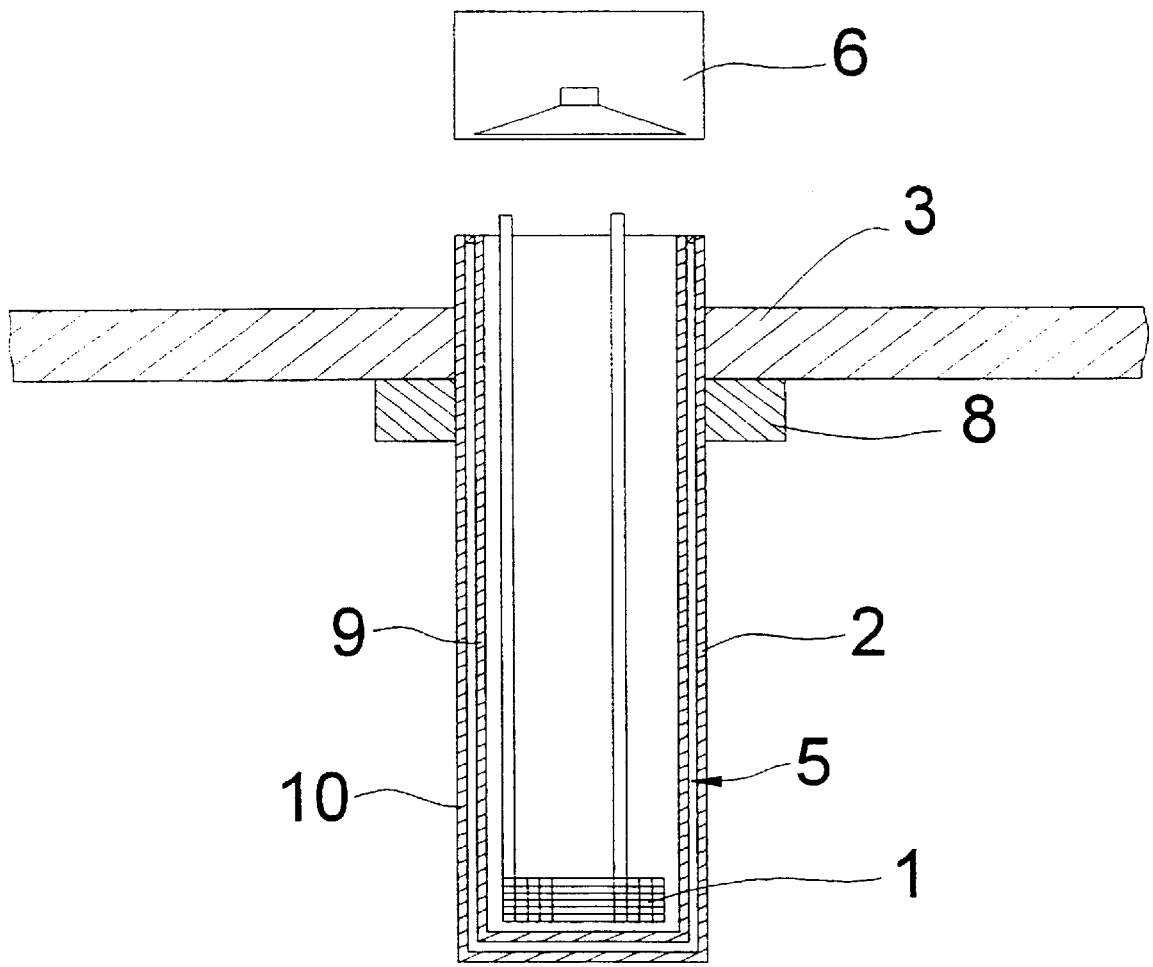
Figure 3:
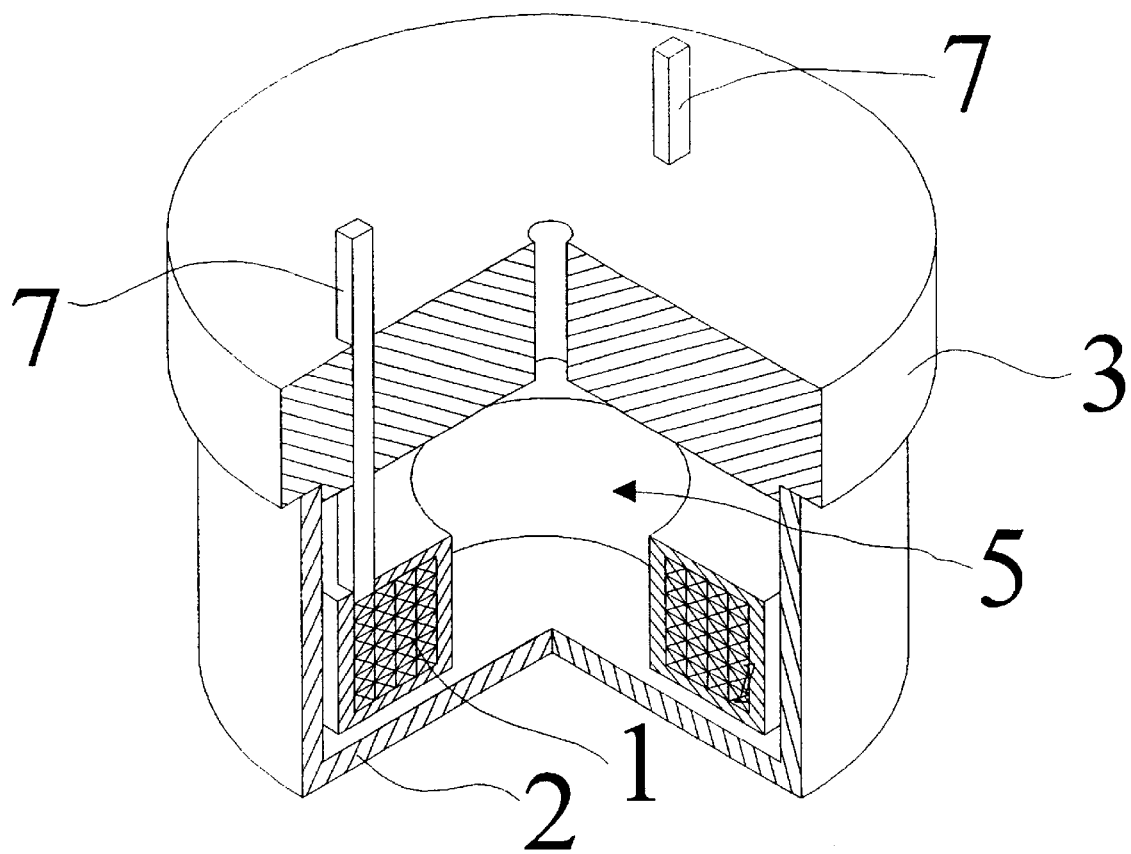

In the following, the invention will be examined in greater detail by making reference to the appended drawings illustrating embodiments of the invention, in which drawings FIG. 1 shows a cross-sectional view of an embodiment of the stimulator head according to the invention;

FIG. 2 shows a cross-sectional view of a second embodiment of the stimulator head according to the invention; and FIG. 3 shows a partially sectional perspective view of a third embodiment of the stimulator head according to the invention.

Referring to FIG. 1, the stimulator head shown therein comprises a coil 1, a housing 2 enclosing said coil, a body piece 3 supporting said housing 2, a cover 4 of said housing 2, an interior space 5 of said housing 2 with facilities permitting said interior space to be brought to a vacuum and electrical conductors 7 suitable for supplying electric energy to said coil 1. Additionally, the stimulator head may include elements not shown in FIG. 1. One of such essential ancillaries required in a plurality of magnetic stimulator types is the cooling piping of the coil 1. In routine operation, the stimulation is carried out using strong currents, whereby running the coil 1 without cooling will cause intense heating thereof if the coil 1 is made from a material exhibiting ohmic losses. One preferred technique of implementing the cooling system is to run the cooling liquid in the interior of the conductors 7, thus also passing the cooling liquid through the interior of the conductors of the coil 1. Hence, the conductors are typically made from hollow pipes. The cooling liquid can be water, for instance.

In the illustrated embodiment, the housing 2 is made elongated, whereby the coil 1 can be disposed at a distance from the housing cover 4 and the equipment body 3. Thus, the object being stimulated, for instance, the head of the examined person or the patient, need not be placed close to the equipment body 3. The distance between the coil 1 and the housing cover 4 is advantageously about 30–100 cm. Then, the mouth of the housing 2 closed by the cover 4 can be located on the opposite side of the equipment body 3 in regard to the test person or the patient into a space which is provided with sound isolation in a conventional manner. By virtue of this construction, it is possible to reduce the sound emissions transmitted toward the patient along the conductors 7 of the coil 1 to the housing cover 4, and therefrom further to the ambient air surrounding the cover 4.

In order to attenuate mechanical vibrations, the feedthrough components of the coil supply conductors 7 mounted on the cover 4 of the housing 2 are advantageously made rigid. Correspondingly, it is advantageous to use a relatively thick and massive housing cover 4, whereby also a long mechanical contact is formed along the conductor feedthrough channels between the conductors 7 and the cover 4. Furthermore, the equipment body 3 is advantageously made massive. Then, the amplitude of vibrations can be reduced by supporting the housing 2 to a massive structure represented in the embodiment by the equipment body 3. Also the seals between the housing 2 and its cover 4, as well as those passing the conductors 7 through the cover 4, must be made airtight. Advantageously, the housing cover has a design which is self-sealing under the applied vacuum.

The housing 2 itself is made from a material which is inherently air-tight and resistant to buckling under the vacuum applied to its interior. Furthermore, the housing 2 must be magnetic-field-transparent at least for those parts which are located close to the coil 1 thus remaining during stimulation between the coil 1 and the tissue being stimulated. In a practical embodiment, the housing 2 can be made from, e.g., a woven/spun glass fiber reinforced material that is coated with a gas-tight material such as a thin metallic layer. Alternatively, the housing 2 can be fabricated from a suitable plastic or glass. In some applications, the housing is advantageously made into a multilayer composite construction having sound-transmission-attenuating elements integrated in the wall of the housing 2.

The coil 1 and the conductors 7 connected thereto are isolated acoustically from the housing 2 by means of taking the gas pressure in the interior space 5 of the housing 2 to a sufficiently low level. Then, the sound insulation is based on the small amount of medium that can transmit vibrations from the coil 1 to the housing 2. Thence, the pressure prevailing in the interior space 5 of the housing must be brought to such a low level that offers sufficient attenuation of the sound reaching the ears of the test person/patient from the coil 1. Assuming the sound pressure of the acoustic wave generated by the coil 1 is 120 dB and the ambient noise level in the test room is in the order of 50–60 dB, the required sound insulation is about 60–70 dB. In addition to these sound pressure and attenuation values, the vacuum required to achieve the desired sound attenuation is determined by such factors as, e.g., the construction and placement of the coil 1 in the interior of the housing 2, as well as the design of the housing 2 itself. Generally, the vacuum in the interior space 5 of the housing must be brought to less than 10%, advantageously to less than 0.05%, of the atmospheric air pressure. Particularly advantageously, the pressure in the interior of the coil housing is less than 0.02 Pa. In fact, this pressure level is in the same order as the absolute sound pressure of 60 dB noise. Hence, the magnitude of sound (that is, the sound pressure) travelling through a gas at a pressure of 0.02 Pa cannot exceed a sound pressure level of about 60 dB. In addition to the sound transmission capability of the gaseous medium, the emitted acoustic energy is related to the acoustic coupling between the coil 1 and the surrounding medium and between the medium and the housing 4.

The stimulator head shown in FIG. 2 has certain details designed slightly different from those of the stimulator head illustrated in FIG. 1. In the stimulator head of FIG. 2, the housing 2 is comprised of an inner shell 9 and an outer shell 10, both being connected to each other in an air-tight manner. In this embodiment, the vacuum required for sound insulation is applied to the inter-shell space between the shells 9, 10 of the housing 2. This embodiment also disposes with the air-tight cover 4 of the housing 2 used in the embodiment shown in FIG. 1. Herein, the mouth of the housing 2 is left uncovered so as to open into a sound-insulated chamber located in the interior of the equipment body 3. Into this chamber, in the vicinity of the mouth of the housing 2, there is placed an active anti-noise generator serving to emit acoustic waves with an anti-phased sound pressure pattern optimized to provide maximal cancellation of the acoustic waves emitted by the coil 1. Provided that the anti-noise generator is capable of attaining sufficient active elimination of the acoustic wave caused by the coil 1, a sound insulation of reduced attenuation capability can be used between the mouth of the coil housing 2 and the patient. Additional attenuation of the vibrations of the housing 2 has been accomplished in the embodiment of FIG. 2 by mounting an attenuating mass 8 on the outer shell 10 of the housing 2.

In FIG. 3, the stimulator head shown therein differs from that of FIG. 1 by having the housing 2 of the stimulator head of FIG. 3 made essentially shorter. This kind of construction is required in, e.g., magnetic stimulators which simply do not allow the use of a stimulator head of any greater length.

Not being limited to the above-described embodiments, alternative constructions may be contemplated without departing from the scope and spirit of the present invention. For instance, the stimulator head can be provided with a relatively large mass connected to the coil 1 in a manner capable of attenuating the vibrations of the coil 1. Furthermore, the number of coils 1 in the same housing 2 may be two or more, whereby the shape of the coils may be varied from that shown in the drawings. One alternative shape of the coil 1 is a so-called figure-of-8 coil wound in the shape of figure eight. For improved serviceability, the housing 2 can be designed for easy replacement of the coil(s) 1. The housing 2 may be complemented with a vacuum gauge and a valve permitting the monitoring and adjustment of the vacuum in the hermetic interior space 5 of the housing 2 to a desired level.

The stimulator head may also include a control mechanism permitting setting the coil 1 as close as possible to the inner wall of the housing 2 that separates the coil 1 from the object being stimulated, however, without allowing the coil to meet said inner wall. Additionally, the interior space of the housing 2 can be provided with sound energy absorbing elements.

The magnetic stimulator equipment may include a vacuum pump connected to the stimulator head. Thus, the vacuum of the hermetic interior space 5 could be provided, e.g., only for the duration of actual tests. Then, the airtightness requirements of the hermetic interior space 5 can be relaxed without compromising the repeatable efficiency of good sound insulation during test sessions. A conventional single-stage mechanical vacuum pump, for instance, is capable of achieving a vacuum of less than 0.01% of the ambient atmospheric pressure. Using a two-stage system of such pump units, it is possible to reach a vacuum less than 0.0001% of the normal atmospheric pressure. If even a better vacuum is desired, a diffusion pump for instance may be connected in series with the mechanical pump.

Furthermore, the equipment body 3 need not be a definite component associated with the stimulator head or the magnetic stimulator. The housing 2 of the stimulator head may as well be mounted on a partition wall of the test room or any other support structure 3. Then, the stimulator head is connected to the magnetic stimulator unit only via its electrical conductors 7.

What is claimed is:

1. A stimulator head of a magnetic stimulator used in the stimulation of living tissue such as the human brain, said stimulator head including:
   at least one coil suitable for generating a stimulating magnetic field,
   conductors for passing electric current from said magnetic stimulator to said at least one coil, and
   a housing having an interior space, the housing having a cover for closing the housing in such a manner that the interior space of the housing is airtight,
   wherein said at least one coil is located in the interior space of the housing and the housing has a construction that is at least partially transparent to said magnetic field,
   whereby an acoustic insulation can be attained between said at least one coil and an object being stimulated by creating a partial vacuum in said airtight space.

2. A method of attenuating an acoustic wave emitted by a stimulator coil of a magnetic stimulator, comprising:
   providing a housing having an interior space,
   placing the stimulator coil in the interior space of the housing,
   employing a cover to close the housing in such a manner that the interior space of the housing is airtight,
   creating a partial vacuum in said interior space.

3. A method according to claim 2, wherein the step of creating a partial vacuum comprises reducing pressure in said interior space to a level not greater than 0.05% of normal atmospheric pressure.

* * * * *